(12) United States Patent
Bakker et al.

(10) Patent No.: US 11,857,450 B2
(45) Date of Patent: Jan. 2, 2024

(54) STRAP ATTACHMENT AND ORTHOPEDIC DEVICE USING THE SAME

(71) Applicant: Ossur Iceland ehf, Reykjavik (IS)

(72) Inventors: Ryan Bakker, Foothill Ranch, CA (US); Scott Seligman, Foothill Ranch, CA (US); Jared Olivo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 17/193,300

(22) Filed: Mar. 5, 2021

(65) Prior Publication Data

US 2021/0275339 A1    Sep. 9, 2021

Related U.S. Application Data

(60) Provisional application No. 62/986,445, filed on Mar. 6, 2020.

(51) Int. Cl.
*A61F 5/01* (2006.01)

(52) U.S. Cl.
CPC .... *A61F 5/0125* (2013.01); *A61F 2005/0144* (2013.01); *A61F 2005/0167* (2013.01)

(58) Field of Classification Search
CPC ........ A61F 5/01; A61F 5/0102; A61F 5/0104; A61F 5/0106; A61F 5/0109; A61F 5/0111; A61F 5/0123; A61F 5/0125; A61F 2005/0132; A61F 2005/0144; A61F 2005/0165; A61F 2005/0167; Y10T 24/21; Y10T 24/2102; A44B 11/00; A44B 11/05; A44B 11/006; A44B 99/00; A43C 11/165; A41D 13/1245; A61L 15/08
See application file for complete search history.

(56) References Cited

U.S. PATENT DOCUMENTS

| | | |
|---|---|---|
| 3,350,719 A | 11/1967 | McClure |
| 4,241,730 A | 12/1980 | Helfet |
| 4,271,831 A | 6/1981 | Deibert |
| 4,628,916 A | 12/1986 | Lerman et al. |
| 5,042,464 A | 8/1991 | Skwor et al. |
| 5,336,161 A | 8/1994 | Lengyel |
| 5,554,104 A | 9/1996 | Grim |

(Continued)

FOREIGN PATENT DOCUMENTS

| | | |
|---|---|---|
| EP | 1829507 B1 | 12/2000 |
| EP | 2802298 A1 | 11/2014 |

(Continued)

OTHER PUBLICATIONS

International Search Report and Written Opinion from PCT Application No. PCT/US2021/020995, dated Jun. 11, 2021.

(Continued)

*Primary Examiner* — Ophelia A Hawthorne
*Assistant Examiner* — Gina McCarthy
(74) *Attorney, Agent, or Firm* — Workman Nydegger

(57) ABSTRACT

A strap attachment for attaching a strap to a frame member in an orthopedic device including a retainer; a cable connected to the retainer having at least one segment arranged to be adjustably connected to a frame of a device; a connector securable to an end portion of the at least one segment of the cable, the connector arranged to engage the frame.

5 Claims, 7 Drawing Sheets

(56) References Cited

U.S. PATENT DOCUMENTS

| | | | |
|---|---|---|---|
| 5,608,599 | A | 3/1997 | Goldman |
| 5,658,243 | A | 8/1997 | Miller et al. |
| 5,891,068 | A | 4/1999 | Kenney |
| 5,947,913 | A | 9/1999 | Palumbo |
| 6,331,169 | B1 | 12/2001 | Bastyr et al. |
| 6,527,733 | B1 | 3/2003 | Ceriani et al. |
| 7,410,471 | B1 | 8/2008 | Campbell et al. |
| 7,597,674 | B2 | 10/2009 | Hu et al. |
| 7,749,183 | B2 | 7/2010 | Ingimundarson et al. |
| 8,043,244 | B2 | 10/2011 | Einarsson et al. |
| 8,657,772 | B2 | 2/2014 | Einarsson |
| 8,936,560 | B2 | 1/2015 | Lunau et al. |
| 2005/0209541 | A1 | 9/2005 | Kenney |
| 2005/0273025 | A1* | 12/2005 | Houser .............. A61F 5/0123 602/5 |
| 2008/0195013 | A1 | 8/2008 | Ingimundarson et al. |
| 2008/0208095 | A1 | 8/2008 | Kazmierczak et al. |
| 2010/0121242 | A1 | 5/2010 | Chiang |
| 2010/0331750 | A1* | 12/2010 | Ingimundarson ..... A61F 5/0102 602/26 |
| 2011/0167546 | A1 | 7/2011 | Olson |
| 2012/0016283 | A1 | 1/2012 | Hollister et al. |
| 2013/0184628 | A1* | 7/2013 | Ingimundarson ...... A44B 99/00 602/26 |
| 2015/0005685 | A1* | 1/2015 | Chetlapalli ........... A61F 5/0125 602/16 |
| 2015/0320581 | A1 | 11/2015 | Causse |
| 2016/0051389 | A1 | 2/2016 | Seligman |
| 2016/0120267 | A1* | 5/2016 | Burns ................. A43C 11/165 24/68 C |
| 2016/0250058 | A1 | 9/2016 | Frangi et al. |
| 2018/0116852 | A1 | 5/2018 | Petursson et al. |
| 2019/0313722 | A1* | 10/2019 | Liu .................... A41D 13/1245 |
| 2019/0374671 | A1* | 12/2019 | Seligman ................ A61L 15/08 |

FOREIGN PATENT DOCUMENTS

| | | |
|---|---|---|
| JP | H11-504530 A | 4/1999 |
| WO | 9620659 A1 | 7/1996 |
| WO | 2005107659 A2 | 11/2005 |
| WO | 2013052358 A1 | 4/2013 |
| WO | 2019241201 A1 | 12/2019 |

OTHER PUBLICATIONS

International Search Report and Written Opinion from PCT Application No. US2019/036480, dated Dec. 4, 2019.

* cited by examiner

STRAP ATTACHMENT AND ORTHOPEDIC DEVICE USING THE SAME

CROSS-REFERENCE TO RELATED APPLICATIONS

This application claims priority to and the benefit of U.S. Provisional Application No. 62/986,445, filed Mar. 6, 2020, and incorporated herein by its entirety. This application also incorporates by reference U.S. Patent Application Publication 2019/0374671, published on Dec. 12, 2019, in its entirety.

FIELD OF THE DISCLOSURE

The disclosure relates to a strap attachment for an orthopedic device and an orthopedic device for using the strap attachment, and, more generally, relates to means for attaching features, such as straps, to a structure in an orthopedic device or other suitable devices.

BACKGROUND

Orthopedic devices or braces comprise a broad range of structures and devices used for supporting or stabilizing a joint when worn on the body of a user. Orthopedic braces may serve in either preventive or remedial roles. In the preventive role, the orthopedic brace can provide additional support, stability, and protection to a healthy joint to prevent or minimize injury to the joint due to undue stress. In the remedial role, the orthopedic brace can support and strengthen a joint weakened due to injury or infirmity and reinforce the vulnerable joint to prevent further injury, correct or assist the infirmity, or facilitate healing joint.

A predominant orthopedic brace is a knee brace, which is used to stabilize the knee by preventing the knee's excessive movement or facilitating the movement of the knee. Many knee braces comprise a frame and have hinges on at least one of the lateral and medial sides of the knee joint. Straps are used to secure the brace to the leg or knee. An injured knee can fit with an "off-the-shelf" brace or with a "custom-fit" brace, with the brace's selection depending on the size and shape of an individual's leg. A clinician may further form either type of braces by providing the frame with malleable materials to customize the frame to the user.

As shown in FIG. 1, an exemplary knee brace 11 typically includes a frame 12 that comprises at least one support member 12a, 12b. When there are multiple support members 12a, 12b corresponding to the upper leg UL and lower leg LL, the knee brace 11 may include rotational hinges 14 that assist and control the movement of the knee K. Suitable straps 16a, 16b depend on strap attachments 10 (the inventive strap attachments, while depicted in FIG. 1, are described in more detail in the detailed description) and may maintain the knee brace 11 on the limb. Other features such as pads may relieve the pressure of the knee brace 11 on the limb and surrounding areas.

Many knee braces reduce knee instability following an injury, counteract fatigue, and treat the impairment of the knee, particularly if the knee has damaged ligaments. Braces may be recommended for walking, skiing, running, twisting, pivoting, or jumping activities. Besides providing increased stability to the knee, knee braces may also decrease the risk of injuring the knee or leg or may assist the knee. One way of protecting the knee is by including attachments such as a patella-protector assembly, which may be secured onto the knee brace and configured to operate to protect the patella from impact during physical activities.

To maximize its supportive, protective, and comfort-related aspects, it is desirable that a knee brace securely and precisely fits the user's leg. While custom-fit braces are made to intimately conform to the precise geometry and dimensions of a leg of a user, it is typical for the geometry and dimensions of the leg to change over time due to weight change, muscle change, inflammation, medical conditions, or other factors, requiring even a custom-fit brace to accommodate many geometries of the leg. As for off-the-shelf braces, these braces must be configurable to suit many leg geometries generally, despite a particular leg's geometry. There is a need for braces that accommodate a user's dynamic dimensions.

Existing braces further fail to account for the geometrical and dimensional variations between different parts of a leg, e.g., the difference in shape between the calf and the shin. Certain areas of the leg require more accommodation from the brace than others, but most braces have only flat frame components and thus fail to address this need.

In recognizing the need for effective knee braces, various knee braces have been introduced into the marketplace. However, such knee braces have generally comprised relatively heavy, bulky apparatuses that fail to provide ventilation and evenly distribute pressure from the brace on the leg of the user. Many contemporary braces are deficient because the braces are constructed such that they lack or do not consistently provide adjustment features for forming a firm, comfortable, and secure interface between the unique and dynamic dimensions of the leg and knee of the user and the brace. Because of these drawbacks, many knee braces detract from the user's endeavor.

For example, some strap supports may be deficient because they add to the brace's bulk by jutting out from the frame with a rigid strap support structure. These features may cause discomfort for a user, increasing the brace's size, profile, and weight, increasing the cost to a user, and making the brace cumbersome to use because of the brace's larger size. Such straps may further increase the risk of damage to the brace and discomfort for a user if, for example, the outwardly jutting straps catch on objects or clothing. The strap attachments' adjustability may be bulky as they may be constructed of plastic to reduce weight, yet sized large to avoid fracture due to tensioning of straps.

Because of their size and to conform to a user's anatomy, conventional strap attachments may protrude a distance from the brace frame, which may lead to poorly fitting on users, especially users with smaller limb dimensions. Strap attachments are often sized the same regardless of a user's brace size. It is not readily understood to modify the sizing of strap attachments to accommodate a user's limb size.

These and other features, aspects, and advantages of the disclosure will become better understood regarding the following description, appended claims, and drawings.

SUMMARY

To accommodate and attach features, such as straps, to an orthopedic device, attaching the features may secure to a frame thereof and generally correspond in strength to the frame assembly's strength. According to an embodiment, a strap attachment or D-ring is provided in a streamlined manner to mitigate or minimize a strap attachment protruding from the frame without compromising the strap attachment's strength. Due to the strap attachment construction, the strength is enhanced over conventional strap attachments in that the embodiment comprises a cable pivotally secured to the frame. The strap attachment may include a coaxially arranged tube along at least a segment of the length of the cable, so the tube may rotate about the cable to accommodate the movement of a strap tethered thereto. The cable may be constructed from an elongate element such as a wire or braided cable, and both the cable and the tube may be formed from metal.

The embodiments of the strap attachment can better yield or conform to the anatomy or movement of a user's limb, as cable segments can articulate relative to the frame. The strap attachment may be retracted or extended relative to the frame, thereby increasing or decreasing a distance a body carried by the cable of the strap attachment extends from the frame. Such variable distance is advantageous, for example, when adjusting or securing a strap to the strap attachment.

The strap attachment's embodiments enable a manufacturer or orthotist to adjust the degree by which the strap attachment extends from a frame element. The embodiments enable a strap attachment and thus, the strap to protrude minimally from an edge of an orthopedic device frame. This arrangement enables the strap attachment to be better suited for smaller orthopedic devices and conform more closely to a user's anatomy. The strap attachment according to the embodiments is arranged more closely in line with the frame of an orthopedic device, devoid of a protrusion at a patient interface surface and a protrusion on an outer profile orthopedic device, offering a lower profile design and comfortable fit. There is less possibility of coming into contact with a user's skin and objects that the orthopedic device may inadvertently strike. With these advantages, the strap attachment has higher strength components, such as a braided cable, than conventional strap attachments.

These and other features, aspects, and advantages of the disclosure will become better understood regarding the following description, appended claims, and drawings.

DETAILED DESCRIPTION OF VARIOUS EMBODIMENTS

Figure 1:
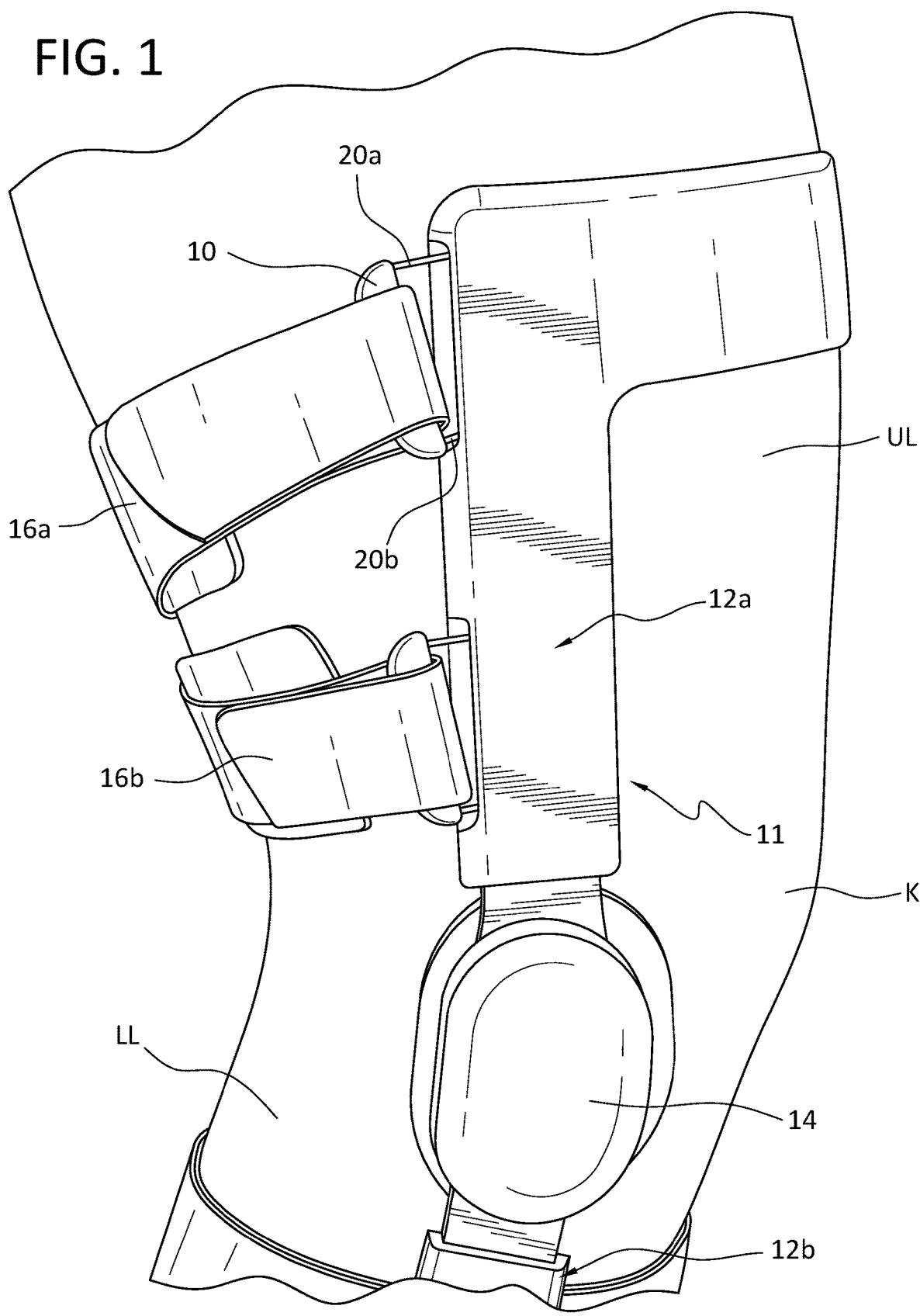
FIG. 1 depicts an orthopedic device in the form of a knee brace.

A better understanding of the disclosure's different embodiments may be had from the following description read with the drawings in which like reference characters refer to like elements.

While the disclosure is susceptible to various modifications and alternative constructions, certain illustrative embodiments are shown in the drawings and are described below. It should be understood, however, there is no intention to limit the disclosure to the specific embodiments disclosed, but on the contrary, the aim is to cover all modifications, alternative constructions, combinations, and equivalents falling within the spirit and scope of the disclosure.

Numerical qualifiers (i.e., first, second, etc.) are used in the following discussion merely for explanatory purposes. They are not intended to limit their location or the number of segments or components of the embodiments.

In these embodiments, the strap attachment is intended to be used in place of a standard D-ring conventionally used in orthopedic devices. A standard D-ring serves as a point of attachment from the strap to the frame of the orthopedic device to hold the brace to the user. It allows for adjustment of strap tension by pulling the strap through an opening formed by the D-ring.

Figure 3A:
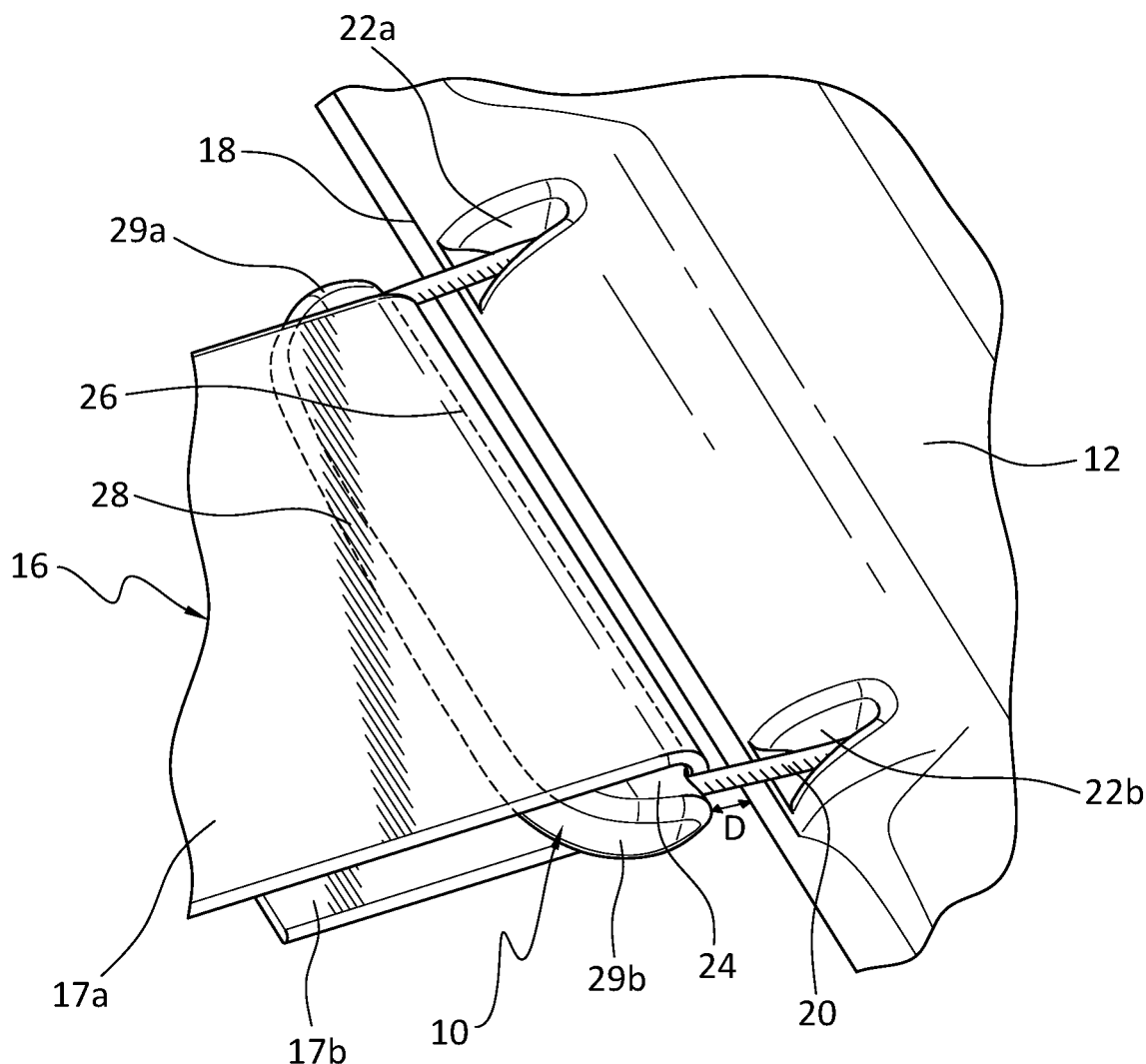
FIG. 3A is a perspective view of the strap attachment in FIG. 2 with a strap attached thereto.
Figure 3B:
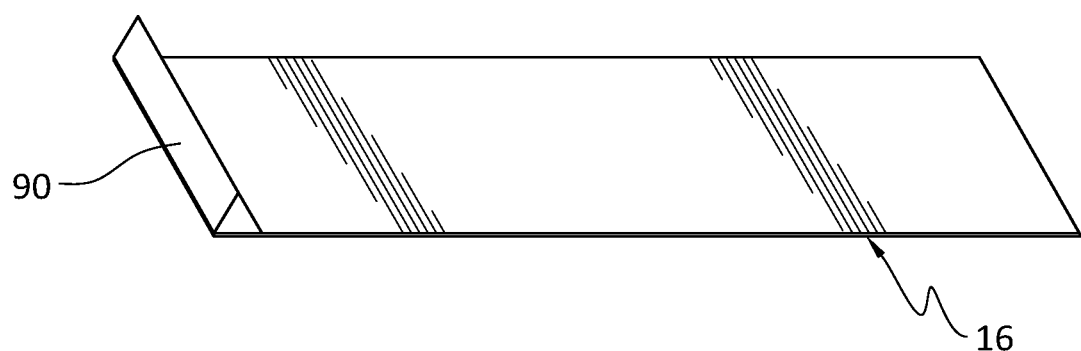
FIG. 3B is a perspective view of a strap useable with the strap attachment of FIG. 2.
Figure 3C:
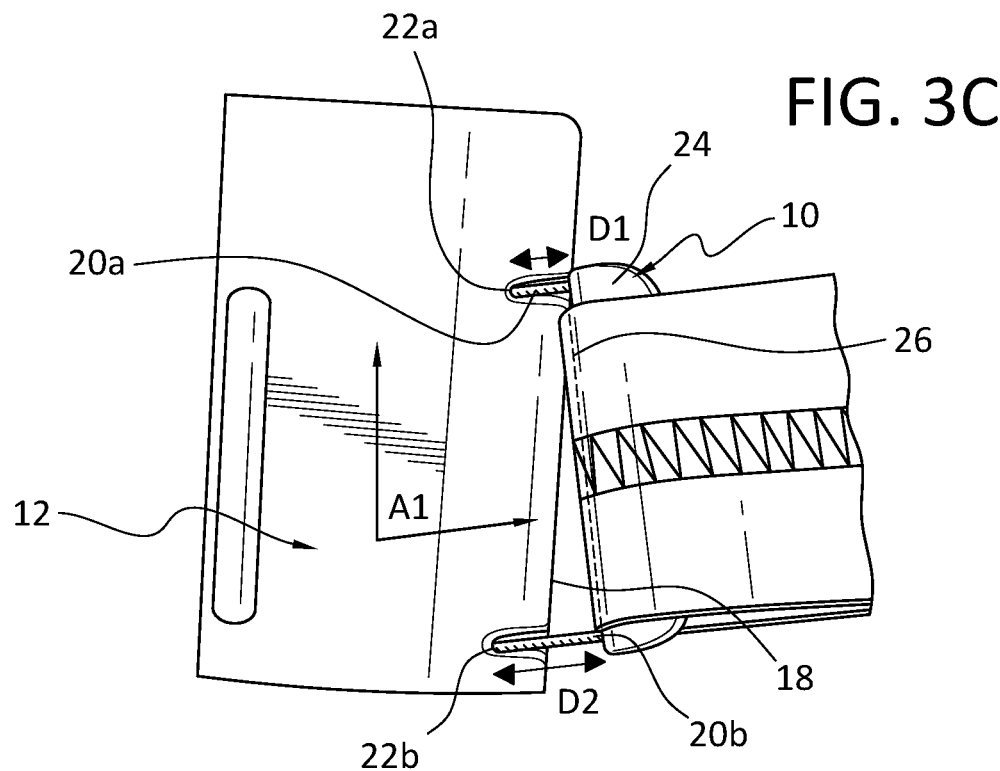
FIGS. 3C and 3D are schematic views of moving the strap attachment at various angles relative to an orthopedic device frame.
Figure 3D:
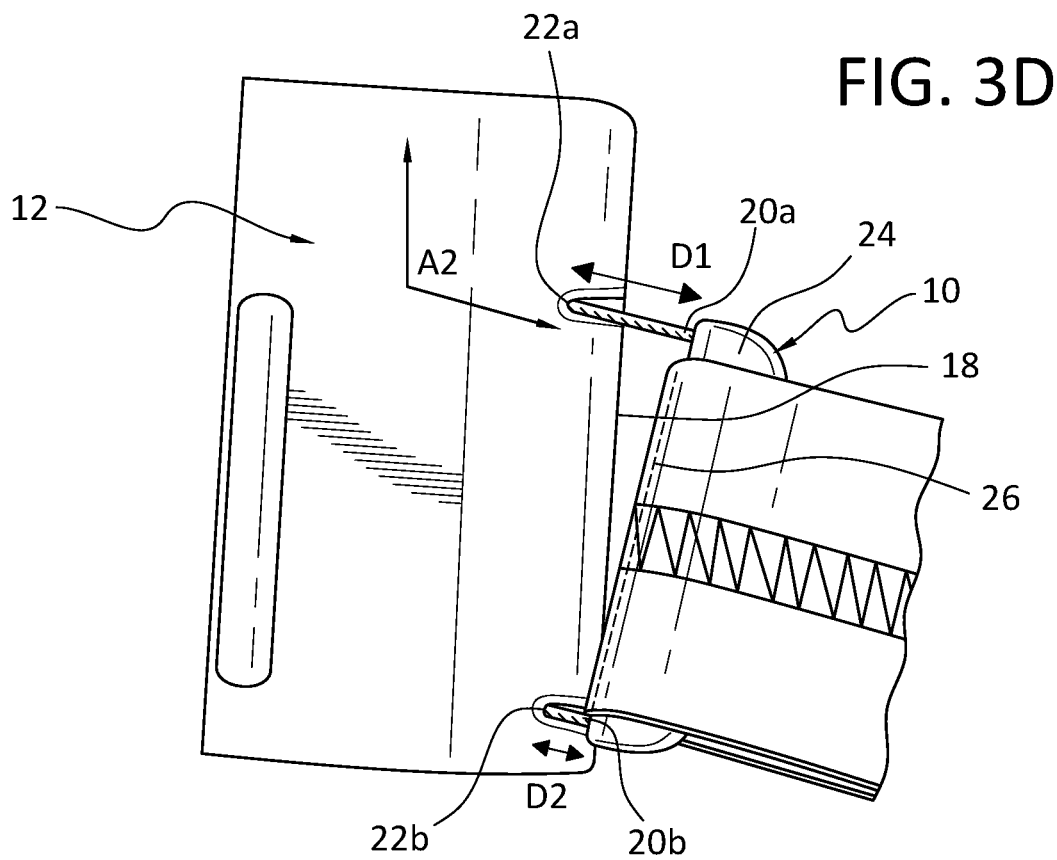

According to the embodiments, as shown in FIGS. 3C and 3D, the strap attachments can articulate to allow for strap articulation to accommodate for different anatomy. As seen in FIG. 1, articulation of the strap attachment allows for the strap to contour to the user's thigh by angling downward. As illustrated in FIG. 3A, the strap attachment can be articulated outward from the patient to allow for the user to easily slip the strap through the slot while minimizing the distance D the strap attachment extends from an edge 18 of the frame of the orthopedic device. This arrangement can be difficult on traditional D-rings as the plastic forming such D-rings can be stiff.

Figure 2:
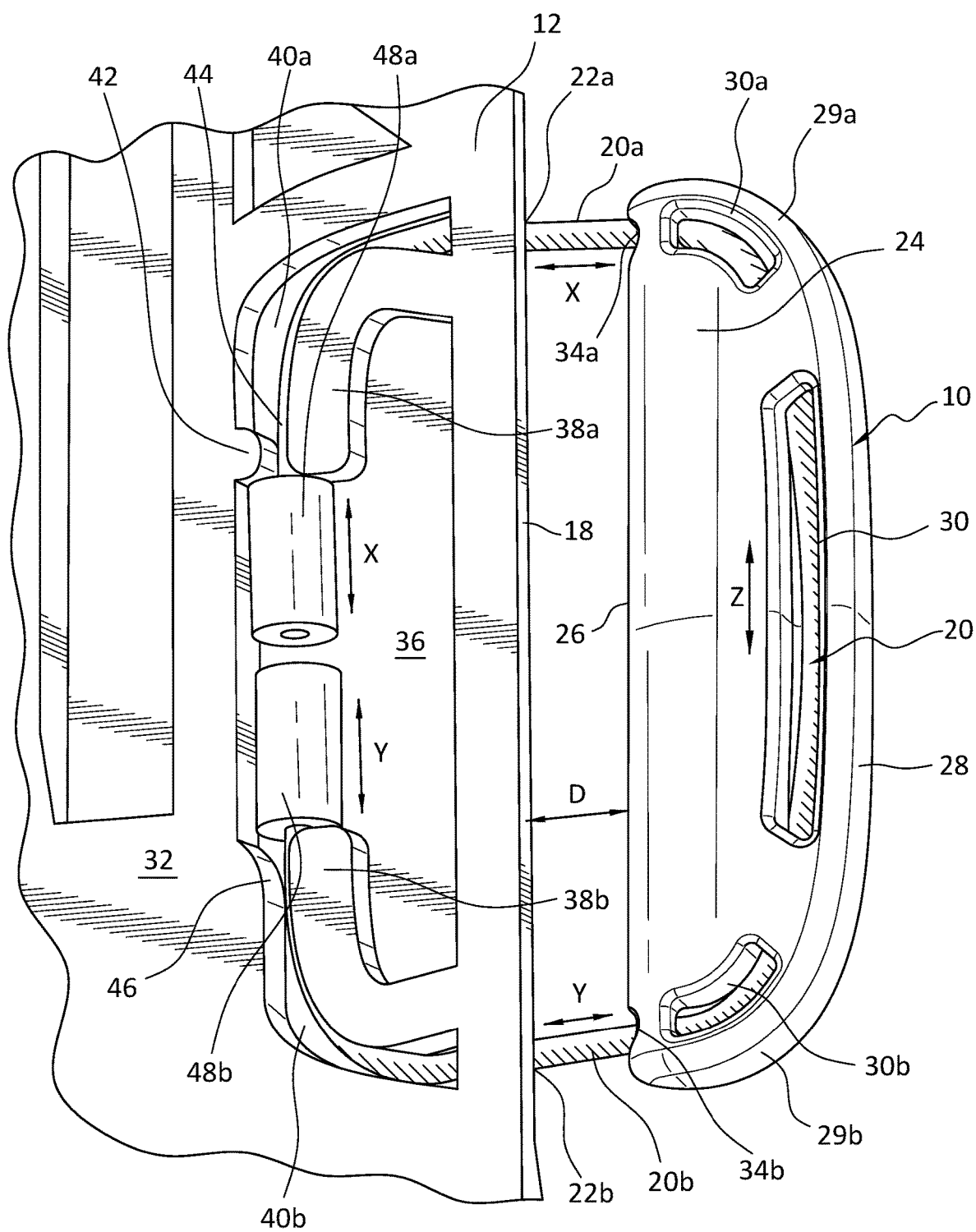
FIG. 2 is a perspective view of an embodiment of a strap attachment of the disclosure.

FIG. 2 shows an embodiment of a strap attachment, and accommodations provided by a frame 12 of the orthopedic device. The strap attachment 10 includes a retainer or body 24 suspended from the frame 12 by a cable 20. The cable 20 extends through retainer 24 with first and second segments 20a, 20b of the cable 20 extending from the retainer 24 to secure to the frame 12. The retainer 24 is preferably arranged a variable distance D from an edge 18 of the frame, permitting adjustability, such as angular and distance, relative to the frame 12, as discussed with FIGS. 1, 3A, 3C, and 3D.

A connector 48 may securable to an end portion of each of the first and second segments 20a, 20b. The connector 48 may be arranged to engage the frame 12 to limit the extension of the segments 20a, 20b from the frame 12. FIG. 2 depicts each end portion of the first and second segments 20a, 20b, including a connector 48a, 48b. In contrast, FIG. 4A discloses a single connector 60 securing both ends of the first and second segments 20a, 20b, as in U.S. Patent Application Publication 2019/0374671. In either of the embodiments of FIGS. 2 and 4A, the first and second segments 20a, 20b may move within a cavity 36, 37 defined by a frame body 32, 33, to extend their distances individually X, Y from the frame edge 18.

In the embodiments, the connectors may permanently crimp ends of the cable or may be removable for further adjustment. The cavities shown may be accessible from inside the frame so the travel and length of the cable can be adjustable and field serviceable.

The retainer 24 defines an inner surface 26 arranged proximate to an edge of a frame 12. The inner surface 26 is adapted for wrapping a strap 16 thereabout. The retainer 24 also defines an outer surface 28 opposite the inner surface 26. The outer surface preferably has rounded edges 29a, 29b leading to the inner surface 26. The rounded edges 29a, 29b avoid the retainer 24 from catching on objects.

In the illustrative example of FIG. 3A, a first segment 17a of a strap 16 is adapted to wrap about the inner surface 26, and a second segment 17b extends past the first segment 17a to secure to the first segment 17a past the outer surface 28. The strap 16 is biased about the inner surface 26, with the rounded edges 29a, 29b extending outside of the strap 16. The outer surface 28 may be arcuate to minimize sharp edges and facilitate application of the strap 16 on the retainer.

The retainer 24 is preferably formed from plastic to reduce weight but is load bearing and preferably rigid to not yield when a strap is tensioned thereabout or therefrom. The retainer 24 is generally thicker and broader than a structural feature about which a conventional D-ring provides for wrapping a strap thereabout, particularly when the retainer 24 is considered combined with the cable 20 extending therethrough. The retainer 24 provides rigidity so a strap can be biased thereabout, whereas a cable would collapse. The retainer advantageously provides sufficient strength to anchor the strap on the user without jutting outwardly by an inconvenient amount. This minimizes the profile of the orthopedic device.

According to variations, the retainer need not be molded, but can be provided as described in U.S. Patent Application Publication 2019/0374671. For example, the retainer may be formed as a metal tube, machined metal, or plastic part, or any other means of creating a flat surface for the strap to wrap around.

While shown in FIG. 2 having two open ends, the cable 20 can alternatively be a continuous loop. The cable 20 may be formed from an elongate element such as a wire or a braided cable and may be formed from metal or polymeric material such as nylon. The cable may be replaced with a tubular member having a continuous structure formed or shaped as a loop to accommodate a tube or be provided with or without such a tube.

As shown in FIG. 2, the retainer 24 defines an internal channel 30 arranged for the cable 20 to extend therethrough. The internal channel 30 defines at least one section 30a, 30b arranged to redirect the cable 20 from a first direction X, Y entering the retainer 24 to a different direction Z generally parallel with the inner surface 26. In this manner, the cable 20 can extend continuously through the retainer 24. The retainer 24 defines first and second apertures 34a, 34b through which the cable 20 extends into the internal channel 30.

In a variation of the embodiments, the cable can comprise two discrete segments that are not continuous with one another but individually attach at portions of the retainer; for example, each extending through a respective first and second aperture. Each cable segment has first and second terminal ends, with the first end secured to the frame and the second end secured to the retainer. From this variation, over two cable segments may secure the retainer to the frame.

FIG. 2 shows the first and second segments 20a, 20b extending at their maximum, so the connectors 48a, 48b are both biased against portions of the frame within the cavity 36. In this configuration, the distance D of the inner surface 26 of the retainer 24 is generally uniform relative to the frame edge 18 and is, therefore, parallel therewith. Such a configuration may be arranged as a default when a strap is uniformly pulled or tensioned from the frame. The distance or direction X, Y of the first and second segments 20a, 20b may likewise be parallel and uniform. Generally, however, the internal channel 30 of the retainer 24 may be arranged so the cable 20 circulates through the internal channel 30 at about 180 degrees from entering a first aperture 34a and exiting a second aperture 34b.

As shown in FIGS. 3C and 3D, the first and second segments 20a, 20b may be extended at an acute angle A1 or an oblique angle A2 relative to the frame edge 18, from a neutral position, as in FIG. 3A when the inner surface 26 of the retainer 24 is arranged parallel to the frame edge 18 and spaced the distance D therefrom.

FIG. 3B shows an embodiment of a strap 16 including a stopper 90. The strap 16 may be adapted to extend through a slot (not shown) defined by the frame 12. The slot (not shown) may be sized sufficiently large to permit passage of the strap 16 therethrough, and the stopper 90 may be sized larger than the slot (not shown) to prevent passage therethrough.

The frame 12 may be arranged with at least one or first and second openings 22a, 22b through which the first and second segments 20a, 20b of the cable 20 extend. As shown in FIG. 3A, the at least one opening 22a, 22b may be configured with a taper and arranged for angular displacement of the first and second segment 20a, 20b relative to the edge 18 of the frame 12.

In a variation, the at least one opening 22a, 22b can be oriented in any suitable direction. For example, the at least one opening 22a, 22b can be formed to allow for the cable to exit the frame from the frame edge perpendicularly, or at diverging or converging orientations.

The openings need not be the width of the cable, and may be flared toward the frame edge, as generally depicted in FIG. 3A. Alternatively, the cable may extend from a single opening, such as one that flares toward the edge and separates the cable into diverging directions. Changing the position and directions of openings can changes how much articulation and strap clearance are allowed. In another variation, a diverter may be installed in the opening to regulate variability so it slidably secures on the cable to fit within the opening to fix a length of the cable that extends from the frame and/or reduce the angular adjustability of the cable relative to the frame edge. The opening can be arranged so that only a single cable segment extends from the frame to the retainer.

In a variation, the frame may include means, such as a recess or channel into which ends of the cable may secure. For example, the frame may be devoid of the aforementioned cavity, but have attachment means located, such as recesses, along the edge of the frame for securing the cable generally externally along the frame. In another variation, ends of the cable may be secured by fasteners to the frame, either individually or by a central fastener. In these ways, it is unnecessary to form the frame with cavities. A connector also, as in U.S. Patent Application Publication 2013/0331751, published Dec. 12, 2013, can be used to which the cable is secured to the frame in a field serviceable manner with a strap tab and fastener.

FIG. 2 shows the frame 12 with a body 32 defining a cavity 36 arranged for receiving the first and second connectors 48a, 48b. The body 32 forms at least one or first and second guide segments 38a, 38b about which the cable 20 extends. The first and second connectors 48a, 48b are adapted to bias against the at least one guide segment 38a, 38b to prevent the cable from coming loose from the frame and detaching the retainer.

The frame body 32 and the at least one guide segment 38a, 38b form channels 40a, 40b sized to permit extension of the cable 20 and prevent extension or escape of the first and second connectors 48a, 48b therefrom. The cavity 36 may be arranged uniformly with the first and second guide segments 38a, 38b arranged similarly, or each of the first and second guide segments 38a, 38b may be arranged at angles and dimensions different from one another, forming differently sized channels relative to one another.

A detent 42 may be provided and protrude from the frame body 32 toward the at least one guide segment 38a, 38b to define a first narrowed channel 44 more narrow than the channels 40a, 40b. The at least one guide segment 38a, 38b may be cantilevered from the frame body 32 into the cavity 36 to form a second narrowed channel 46 more narrow than the at least one channel 40a, 40b. Various configurations may channel or guide the first and second segments 20a, 20b or the cable 20 generally within the frame, and narrowed sections may be provided to crimp or control movement of the cable 20.

Figure 4A:
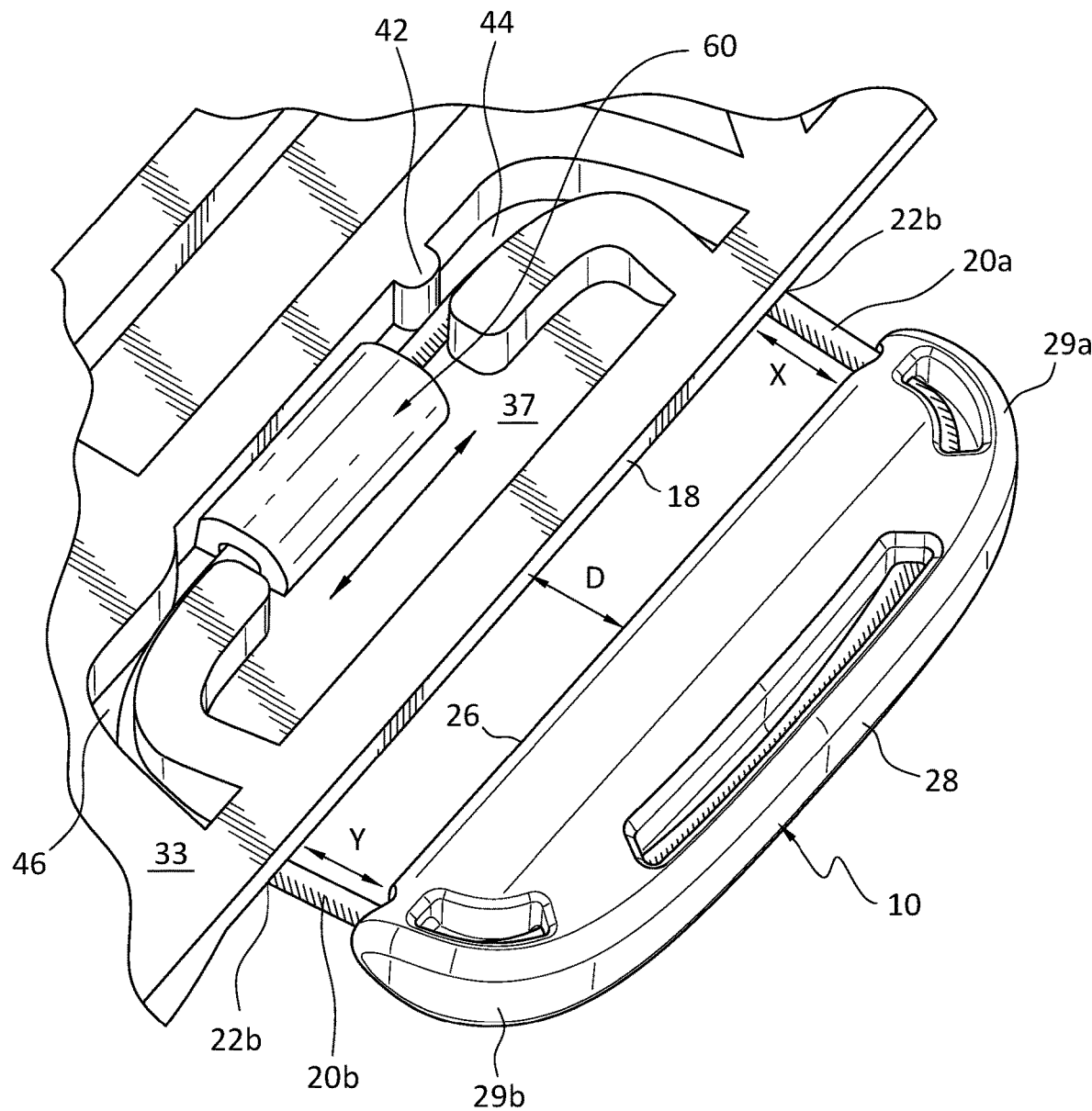
FIG. 4A is a perspective view of another embodiment of the strap attachment.

FIG. 4A illustrates a variation of a cavity 37 of a frame body 33 having a generally uniform configuration, and adapted for the single connector 60 connecting first and second ends of the first and second cable segments 20a, 20b.

Figure 4B:
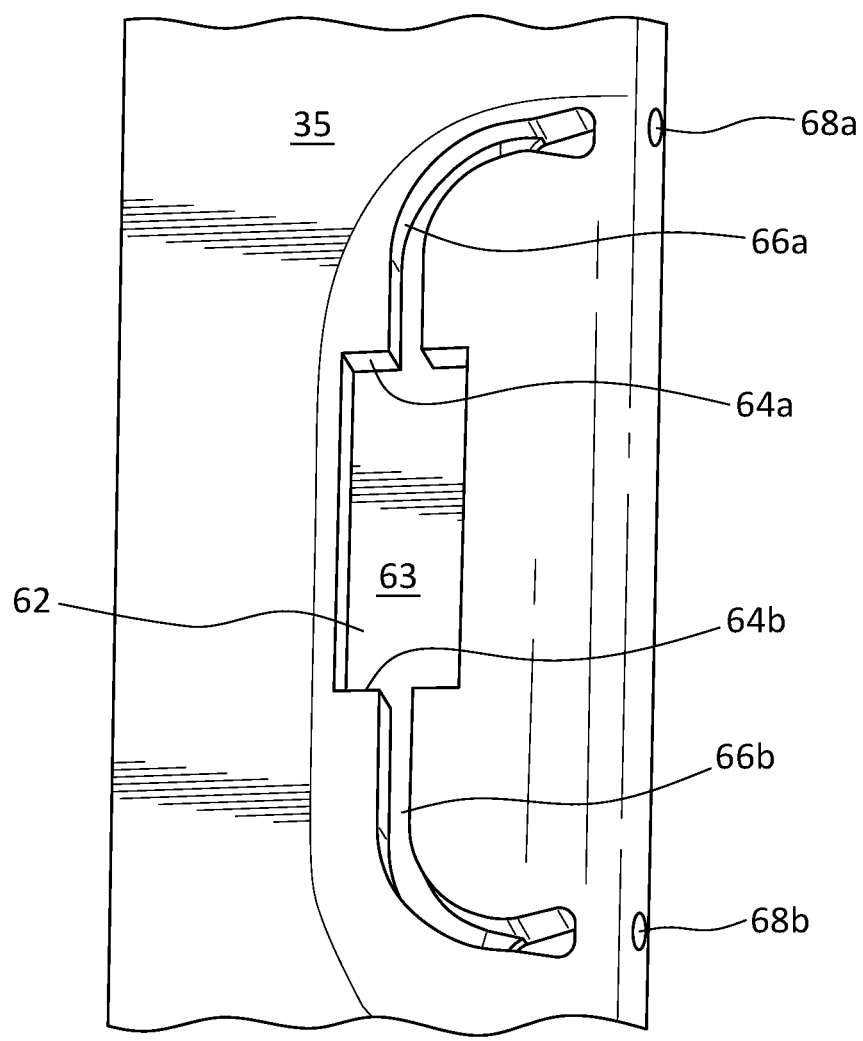
FIG. 4B is a perspective view of a cavity in a frame for accommodating the strap attachment.

FIG. 4B illustrates another variation of a cavity 62 of a frame body 35. The cavity 62 includes a central portion 63 adapted to receive at least one connector and first and second channels 66a, 66b extending to an outlet 68a, 68b adapted for a cable to extend therethrough. The central portion 63 forms first and second stop surfaces 64a, 64b arranged for preventing a connector from passing into the first and second channels 66a, 66b.

Figure 5:
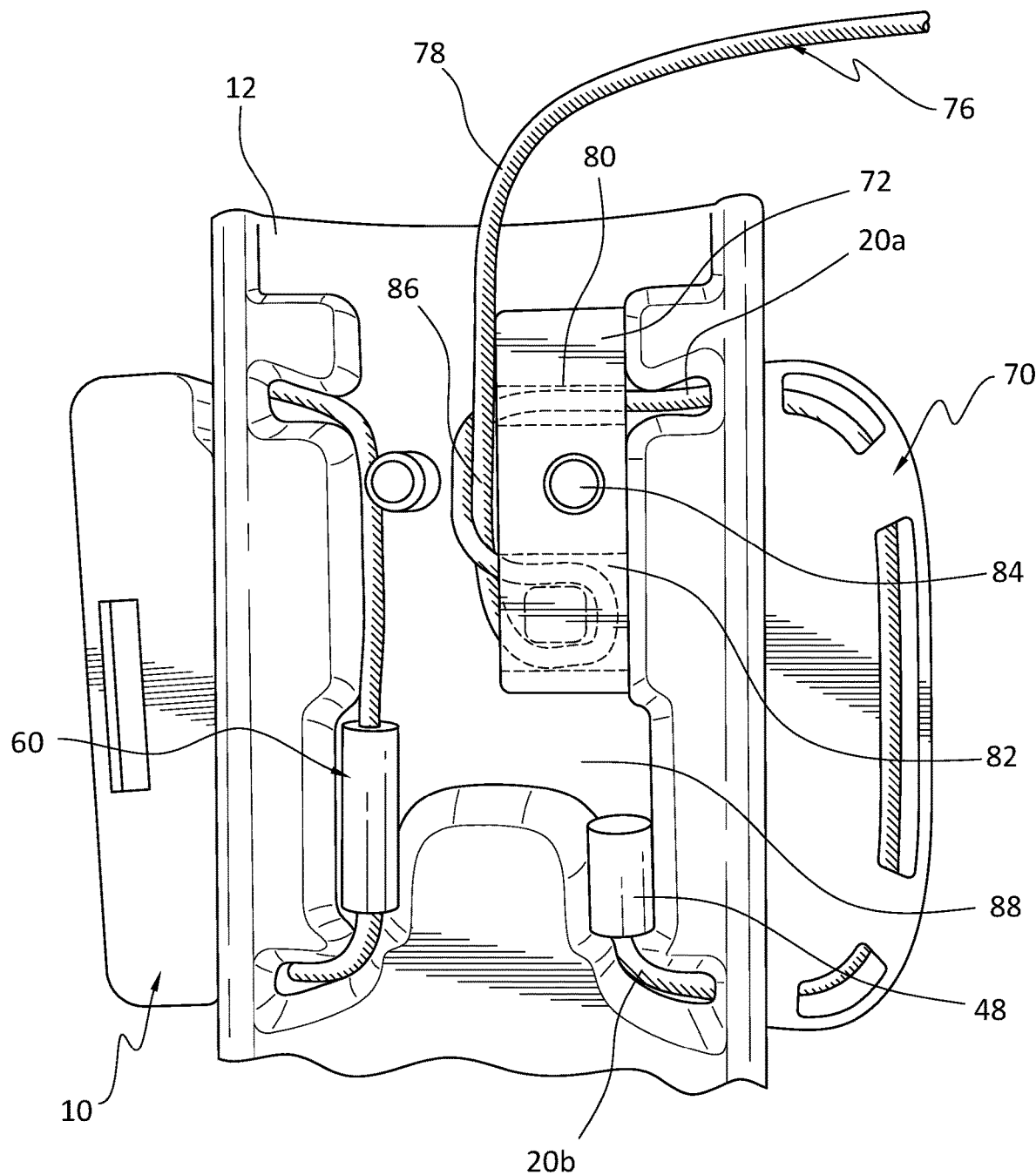
FIG. 5 is a perspective view of another embodiment of a strap attachment.

FIG. 5 illustrates another embodiment of a strap attachment 70. In this embodiment, the strap attachment 70 includes a cable 76 and an adjustable connector 72. The adjustable connector 72 has at least one or first and second channels 80, 82 through which the cable 76 extends. The second segment 20a defines a portion 78 extending past the adjustable connector 72. The cable 76 may be arranged for entering the adjustable connector 72 from outside the frame 12 so the first segment 20a connects to the adjustable connector 72. In contrast, the second segment 20b secures to a connector 48, as in aforementioned embodiments. The portion 78 extends from another side of the adjustable connector 72 so that the second segment 20a is arranged for tying or securing a length 86 against the adjustable connector 72.

As a variation, the portion 78 may extend to a dial tensioning device, as in U.S. Patent Application Publication 2009/0287128, published on Nov. 19, 2009, and incorporated by reference. By the dial tensioning device, there is no tying of the length 86, but it is captured by the dial tensioning device and the length of the cable 76 is regulated according to a desired distance of the retainer relative to the frame edge.

The frame 12 defines a cavity 88 for receiving the adjustable connector 72. The cavity 88, may be formed along an inner side of the frame 12 so that a clinician can access the adjustable connector 72. As in any other embodiments, strap attachments 10, 70 may extend from opposed sides of a frame, sharing a cavity, as in the cavity 88 in FIG. 5. In the depicted example, the orthopedic device may be provided with a strap attachment that is not further adjustable, and an adjustable strap attachment, or both the same. As in the depicted embodiment, the frame 12 provides at least one peg 84 extending in the cavity 88 upon which the strap attachment 70 is secured.

It is to be understood that not necessarily all objects or advantages may be achieved under any particular embodiment of the disclosure. For example, those skilled in the art will recognize that the orthopedic device and strap attachment assembly may be embodied or carried out to achieve or optimize one advantage or group of advantages as taught without achieving other objects or advantages as taught or suggested herein.

The skilled artisan will recognize the interchangeability of various disclosed features. Besides the variations described, other known equivalents for each feature can be mixed and matched by one of ordinary skill in this art to construct an orthopedic device and/or strap attachment under principles of the present disclosure. It will be understood by the skilled artisan that the features described may be adapted to other types of orthopedic devices or other devices used for carrying a strap. Hence this disclosure and the embodiments and variations are not limited to orthopedic devices but can be utilized in any suitable device.

Although this disclosure describes certain exemplary embodiments and examples of an orthopedic device, it, therefore, will be understood by those skilled in the art that the present disclosure extends beyond the disclosed embodiments to other alternative embodiments and/or uses of the disclosure and obvious modifications and equivalents. It is intended that the scope of the present disclosure should not be limited by the disclosed embodiments described above, and may be extended to devices and other applications that may employ the features described.

The invention claimed is:

1. A strap attachment assembly for attaching a strap to a device, comprising:
    a frame member belonging to the device;
    a retainer;
    a cable connected to the retainer having at least one segment arranged to be adjustably connected to a frame of the device, the cable being pivotally secured to the frame; and
    a connector securable to an end portion of the at least one segment of the cable, the connector arranged to engage the frame and to limit extension of the first segment from the frame;
    wherein the frame defines at least one opening through which the cable extends and has a first end portion retained by the frame in said at least one opening;
    wherein the frame has a body defining a cavity arranged for receiving the connector;
    wherein the body defines at least one guide segment within the cavity and about which the cable extends, wherein the connector is adapted to bias against the at least one guide segment;
    wherein the body and the at least one guide segment form at least one channel sized to permit extension of the cable and prevent extension of the connector therein;
    wherein a detent protrudes from the body toward the at least one guide segment to define a first narrowed channel is more narrow than the at least one channel;
    wherein the at least one guide segment is cantilevered toward the body to form a second narrowed channel more narrow than the at least one channel.

2. The strap attachment assembly of claim 1, wherein the at least one opening is configured with a taper and arranged for angular displacement of the at least one segment of the cable relative to the frame.

3. The strap attachment assembly of claim 1, wherein the cable circulates through an internal channel formed by the retainer at about 180 degrees from entering a first aperture and exiting a second aperture.

4. A strap attachment assembly for attaching a strap to a device, comprising:
    a frame member belonging to the device;
    a retainer;

a cable connected to the retainer having at least one segment arranged to be adjustably connected to a frame of the device, the cable being pivotally secured to the frame; and a first connector and a second connector securable to an end portion of the at least one segment of the cable, the connectors arranged to engage the frame and to limit extension of the first segment from the frame;

wherein the frame defines at least one opening through which the cable extends and has a first end portion retained by the frame in said at least one opening;

wherein the frame has a body defining a cavity arranged for receiving the connectors;

wherein the body defines at least one guide segment within the cavity and about which the cable extends, wherein the connectors are adapted to bias against the at least one guide segment;

wherein the body and the at least one guide segment form at least one channel sized to permit extension of the cable and prevent extension of the connectors therein;

wherein a detent protrudes from the body toward the at least one guide segment to define a first narrowed channel is more narrow than the at least one channel;

wherein the cable has first and second segments having the first and second connectors adapted to engage the frame, the first segment being adapted to extend a first distance farther from a frame edge of the frame to the retainer than a second distance measured along the second segment from the frame edge of the frame to the retainer, the first and second segments configured to move within the cavity to individually extend first and second distances, respectively, from the frame edge;

wherein the first and second segments are arranged to extend at an acute angle or an oblique angle relative to the frame edge, from a neutral position, wherein an inner surface of the retainer is arranged parallel to the frame edge and spaced a distance therefrom.

5. An orthopedic device, comprising:

a frame member belonging to the orthopedic device;

a strap connected to the frame member;

a retainer arranged to engage the strap;

a cable connected to the retainer having at least one segment arranged to be adjustably connected to a frame of the orthopedic device, the cable being pivotally secured to the frame;

a first connector and a second connector securable to an end portion of the at least one segment of the cable, the connectors arranged to engage the frame and to limit extension of the first segment from the frame;

wherein the frame defines at least one opening through which the cable extends and has a first end portion retained by the frame in said at least one opening, the at least one opening being configured with a taper and arranged for angular displacement of the at least one segment of the cable relative to the frame;

wherein the frame has a body defining a cavity arranged for receiving the connectors, the body defining at least one guide segment about which the cable extends, the connectors being adapted to bias against the at least one guide segment;

wherein the cable circulates through an internal channel formed by the retainer and oriented at about 180 degrees from entering a first aperture and exiting a second aperture;

wherein the body and the at least one guide segment form at least one channel sized to permit extension of the cable and prevent extension of the connectors therein;

wherein a detent protrudes from the body toward the at least one guide segment to define a first narrowed channel more narrow than the at least one channel;

wherein the cable has first and second segments each having one of the first connector and the second connector adapted to engage the frame, the first segment being adapted to extend a first distance farther from a frame edge of the frame to the retainer than a second distance measured along the second segment from the frame edge of the frame to the retainer, the first and second segments configured to move within the cavity to individually extend first and second distances, respectively, from the frame edge;

wherein the first and second segments are arranged to extend at an acute angle or an oblique angle relative to the frame edge, from a neutral position, wherein an inner surface of the retainer is arranged parallel to the frame edge and spaced a distance therefrom.

* * * * *